United States Patent [19]

Stähle et al.

[11] 4,454,149
[45] Jun. 12, 1984

[54] IMIDAZO[1,2-a]IMIDAZOLES IN THE TREATMENT OF PAIN, HYPERTONIA AND CORONARY DISEASES

[75] Inventors: Helmut Stähle; Herbert Köppe; Werner Kummer, all of Ingelheim; Klaus Stockhaus, Bingen; Wolfgang Hoefke, Wiesbaden; Wolfram Gaida, Ingelheim, all of Fed. Rep. of Germany

[73] Assignee: Boehringer Ingelheim KG, Ingelheim am Rhein, Fed. Rep. of Germany

[21] Appl. No.: 389,283

[22] Filed: Jun. 17, 1982

[30] Foreign Application Priority Data

Jun. 24, 1981 [DE] Fed. Rep. of Germany ....... 3124701

[51] Int. Cl.³ .................. A61K 31/415; C07D 487/04
[52] U.S. Cl. ................. 424/273 R; 544/281; 548/315; 548/324
[58] Field of Search ............ 548/324; 424/273 R

[56] References Cited

U.S. PATENT DOCUMENTS 2,824,879 2/1958 McKay et al. .................. 548/324

Primary Examiner—Richard A. Schwartz
Attorney, Agent, or Firm—Hammond & Littell, Weissenberger & Dippert

[57] ABSTRACT

This invention relates to substituted imidazo[1,2-a]imidazoles and non-toxic, pharmaceutically acceptable salts thereof. These compounds are useful in relieving pain and in treating hypertonia and coronary diseases.

13 Claims, No Drawings

IMIDAZO[1,2-a]IMIDAZOLES IN THE TREATMENT OF PAIN, HYPERTONIA AND CORONARY DISEASES

This invention relates to novel substituted imidazo[1,2-a]imidazoles and non-toxic, pharmaceutically acceptable acid addition salts thereof, to methods of preparing these compounds, to pharmaceutical compositions containing them as active ingredient, and to methods of using them as analgesics, as anti-hypertonic agents, and as cardiac and coronary therapeutic agents.

More particularly, the present invention relates to a novel class of 1-substituted 2-methylene-1H-2,3,5,6-tetrahydro-imidazo[1,2-a]imidazole compounds represented by the formula

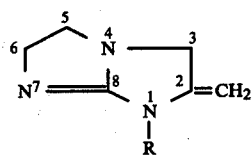
(I)

and non-toxic, pharmacologically acceptable acid addition salts thereof. In Formula I, R represents a phenyl group which is mono-, di-, or trisubstituted by substituents selected from the group consisting of hydrogen, fluorine, chlorine, and bromine atoms and methyl and trifluoromethyl groups, which substituents may be identical or different.

The acid addition salts comprise any desired non-toxic, pharmacologically acceptable salts formed with inorganic or organic acids. Examples of suitable such salts include hydrohalides such as hydrochlorides, sulfates, hydrogen sulfates, phosphates, hydrogen phosphates, tartrates, succinates, maleates, benzoates, acetates, propionates, lactates, ascorbinates, and the like.

The compounds of Formula I can be prepared by thermal cyclization of compounds of the general formula

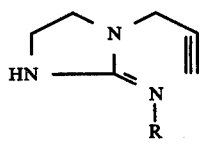
(II)

wherein R is as defined above, at temperatures of from about 60° to 180° C. Thermal cyclization is appropriately effected by heating the compounds of Formula II in the presence of a polar or apolar organic solvent to temperatures of from about 60° to 180° C. The particular temperatures depend on the reactivity of the compound of Formula II employed.

In addition to the compounds of Formula I, the thermal cyclization also yields the isomeric compounds of the general formula

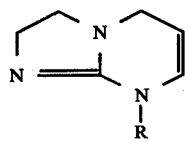
(III)

wherein R is as defined above, which have to be separated. Since the isomers of Formulae I and III differ significantly in their pK values ($pK_I < pK_{III}$), they can easily be separated on the basis of this difference. By fractional extraction of the aqueous solution of a mixture of compounds of Formula I and III at increasing pH values, the less basic compounds of Formula I can be extracted first and thereby isolated, while the more strongly basic compounds of Formula III remain in the aqueous solution.

The substances with a lower pK value, i.e., the compounds of Formula I, have been found to have a higher $R_F$ value than the isomeric compounds of Formula III when investigated by thin layer chromatography (silica gel) in the following systems:

| System | Components | Component Ration |
|---|---|---|
| A | toluene/dioxan/ethanol/concentrated ammonia | 50:40:5:5 |
| B | ethyl acetate/isopropanol/concentrated ammonia | 70:40:20 |
| C | sec.butanol/formic acid (85%)/H$_2$O | 75:15:10 |

The structures of the new imidazo[1,2-a]imidazoles of Formula I have been verified by $^1H$ or $^{13}C$ nuclear resonance and mass spectroscopy.

The starting compounds of Formula II are known and are described in, for example, German published application (DE-OS) No. 25 23 103, incorporated herein by reference.

The imidazo[1,2-a]imidazoles of Formula I according to the invention can be converted into their non-toxic, pharmacologically acceptable acid addition salts in conventional manner. Acids suitable for salt formation include, for example, hydrochloric acid, hydrobromic acid, hydriodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicyclic acid, ascorbic acid, methanesulfonic acid, 8-chlorotheophyllin, and the like.

The compounds of Formula I and the acid addition salts thereof have analgesic, hypotensive, and heart rate-reducing properties. The analgesic effect has been tested using the writhing test in the mouse. Moreover, a measurement of blood pressure in rabbits to which these compounds were administered has shown that the compounds have a hypotensive activity. In view of these properties, the compounds of Formula I may be useful as medicaments for the treatment of pain, hypertonia, and coronary diseases.

The compounds of Formula I can be incorporated, optionally in combination with other active ingredients, into the usual pharmaceutical preparations such as tablets, coated tablets, capsules, powders, suppositories, or solutions. Such preparations may be produced with use of conventional pharmaceutical excipients, carriers, disintegrants, or lubricants or substances for obtaining delayed or sustained release. The single dose for adults is from about 0.1 to 80 mg (from about 0.0013 to 1.07 mg/kg), preferably, however, from about 1 to 30 mg (from about 0.013 to 0.40 mg/kg), 1 to 4 times daily.

Dependent upon the type and body weight of the patient to be treated, on the type and severity of the disease, on the type of preparation, and on the route of administration, which may be peroral, parenteral, or rectal, as well as on the period or interval over which the administration takes place, it may, however, be necessary to deviate from the above dosages. Thus, it may be sufficient in some cases to administer less than the above-mentioned amount of active ingredient or in some cases the amount may be exceeded. The optimum dosage and route of administration of the active ingredients which are necessary in each case can easily be determined by one skilled in the art.

The following examples are intended to illustrate the invention and should not be construed as limiting the invention thereto.

EXAMPLES

The following examples are representative preparations of compounds of Formula I.

EXAMPLE 1

1-(2,6-Dichlorophenyl)-2,3,5,6-tetrahydro-2-methylene-1H-imidazo[1,2-a]imidazole

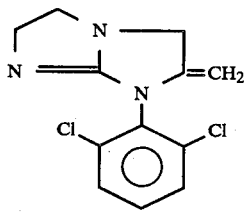

An amount of 5.4 gm of 1-propargyl-2-(2,6-dichlorophenylimino)-imidazolidine was refluxed in 40 ml of ethanol for 10 hours, under stirring. The reaction mixture was then evaporated to dryness in vacuo. The residue was dissolved in 1N HCl, and the resulting solution was fractionally extracted with ether at increasing pH values (rendered alkaline with 2N NaOH). The starting imidazolidine was separated as the first compound (checked by thin layer chromatography). As soon as it had been quantitatively removed, the new imidazo[1,2-a]imidazole derivative was fractionally extracted with ether, as the pH values were progressively increased (slowly rendered alkaline with 2N NaOH in stages; checked by thin layer chromatography). The ether extracts, found to be pure by thin layer chromatography, were combined and dried over anhydrous calcium sulfate, and the ether was eliminated in vacuo.

Yield: 0.85 gm (15.9% of theory);

Melting point: 165°–168° C.

The hydrobromide melted at 203°–204° C.

EXAMPLE 2

1-(2-Bromo-6-fluorophenyl)-2,3,5,6-tetrahydro-2-methylene-1H-imidazo[1,2-a]imidazole

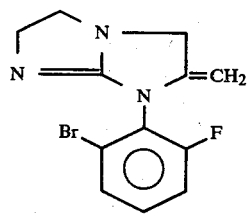

A quantity of 8.9 gm of 1-propargyl-2-(2-bromo-6-fluorophenylimino)-imidazolidine was refluxed in 60 ml of absolute ethanol for about 11 hours. Then the solvent was eliminated in vacuo, and the remaining residue was dissolved in dilute (approximately 1N) hydrochloric acid. The imidazolidine derivative used (identified by thin layer chromatography) was then eliminated by fractional extraction with ethyl acetate at increasing pH values (rendered alkaline with 2N NaOH). As soon as the starting imidazolidine has been quantitatively removed, the imidazo[1,2-a]imidazole derivative according to the invention was extracted as the pH values increased still further (carefully rendered alkaline with 2N NaOH in stages). After being checked by thin layer chromatography, the individual extracts were combined and dried over anhydrous calcium sulfate, and the solvent was eliminated in vacuo.

Yield: 0.6 gm (6.8% of theory);

Melting point: 122°–124° C.

The compounds set forth in the following table were prepared by use of analogous procedures:

TABLE

| Example No. | R | Yield (% of theory) | M.p. (°C.) |
|---|---|---|---|
| 3 | 2-F, 6-CF₃ phenyl | 9.0 | 122–124° |
| 4 | 2,6-Br₂ phenyl | 8.9 | 142–146° |
| 5 | 2-Cl, 6-CH₃ phenyl | 15.4 | 128–130° |
| 6 | 2-Cl, 6-F phenyl | 15.4 | 129–132° |
| 7 | 2,6-Br₂, 4-F phenyl | 13.8 | 126–128° |

TABLE-continued

| Example No. | R | Yield (% of theory) | M.p. (°C.) |
|---|---|---|---|
| 8 | 2,6-dichlorophenyl | 12.4 | 122–124° |
| 9 | 2,3-dichlorophenyl | 18.0 | 119–122° |
| 10 | 2,6-dibromo-4-methylphenyl | 15.2 | 111–113° |

The following examples illustrate a few pharmaceutical dosage unit compositions comprising a compound of the invention as active ingredient.

EXAMPLE 11

Coated Tablets

Composition of one coated tablet:

| Component | Amount (mg) |
|---|---|
| Active ingredient according to the invention | 5 |
| Lactose | 65 |
| Corn starch | 130 |
| Sec. calcium phosphate | 40 |
| Soluble starch | 3 |
| Magnesium stearate | 3 |
| Colloidal silicic acid | 4 |
| Total | 250 |

Preparation

The active ingredient was mixed with some of the excipients, kneaded thoroughly with an aqueous solution of the soluble starch, and granulated in the usual way by means of a screen. The granulate was mixed with the remaining excipients and compressed to form tablet cores weighing 250 mg, which were then coated in the usual way with sugar, talc, and gum arabic.

EXAMPLE 12

Ampules

Composition of one ampule:

| Component | Amount |
|---|---|
| Active ingredient according to the invention | 1.0 mg |
| Sodium chloride | 18.0 mg |
| Distilled water | q.s. ad 2.0 ml |

Preparation

The active ingredient and sodium chloride were dissolved in water, and the resulting solution was transferred into glass ampules under a nitrogen atmosphere.

EXAMPLE 13

Drops

Composition of one vial:

| Component | Amount |
|---|---|
| Active ingredient according to the invention | 0.02 gm |
| Methyl p-hydroxybenzoate | 0.07 gm |
| Propyl p-hydroxybenzoate | 0.03 gm |
| Demineralized water | q.s. ad 100 ml |

Preparation

The active ingredient and preservatives were dissolved in demineralized water, and the resulting solution was filtered and transferred into vials each containing 100 ml.

Any one of the other compounds embraced by Formula I or a non-toxic, pharmacologically acceptable salt thereof with an inorganic or organic acid, may be substituted for the particular active ingredient employed in Examples 11 through 13. Likewise, the amount of the active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

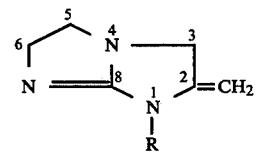

wherein R represents a phenyl group having from 1 to 3 substituents selected from the group consisting of hydrogen, fluorine, chlorine and bromine atoms and methyl and trifluoromethyl groups, the substituents being identical or different, or a non-toxic, pharmacologically acceptable acid addition salt thereof.

2. The compound of claim 1, wherein R is a 2,6-dichlorophenyl group.

3. The compound of claim 1, wherein R is a 2-bromo-6-fluorophenyl group.

4. The compound of claim 1, wherein R is a 2-fluoro-6-trifluoromethylphenyl group.

5. The compound of claim 1, wherein R is a 2,6-bromophenyl group.

6. The compound of claim 1, wherein R is a 2-chloro-6-methylphenyl group.

7. The compound of claim 1, wherein R is a 2-chloro-6-fluorophenyl group.

8. The compound of claim 1, wherein R is a 2,4-dibromo-6-fluorophenyl group.

9. The compound of claim 1, wherein R is a 2,4-dichlorophenyl group.

10. The compound of claim 1, wherein R is a 2,3-dichlorophenyl group.

11. The compound of claim 1, wherein R is a 2,6-dibromo-4-methylphenyl group.

12. A pharmaceutical dosage unit composition for relieving pain or treating hypertonia or coronary diseases consisting essentially of an inert pharmaceutical carrier and an effective amount of a compound of claim 1.

13. A method of relieving pain or treating hypertonia or coronary diseases in a host in need of such relief or treatment which comprises perorally, parenterally, or rectally administering to said host an effective pain relieving or hypertonia or coronary disease treating amount of a compound of claim 1.

* * * * *